United States Patent

Van Der Schaaf et al.

[11] Patent Number: 6,077,805
[45] Date of Patent: Jun. 20, 2000

[54] HEXACOORDINATED RUTHENIUM OR OSMIUM CARBENE CATALYSTS

[75] Inventors: Paul Adriaan Van Der Schaaf, Fribourg; Andreas Hafner, Laupen; Andreas Mühlebach, Belfaux, all of Switzerland

[73] Assignee: Ciba Specialty Chemicals Corporation, Tarrytown, N.Y.

[21] Appl. No.: 09/033,265

[22] Filed: Mar. 2, 1998

[30] Foreign Application Priority Data

Mar. 6, 1997 [CH] Switzerland .................... 0527/97

[51] Int. Cl.[7] ............... B01J 31/00; C07F 15/00; C07F 17/02; C07D 231/00; C07D 233/00
[52] U.S. Cl. .................... 502/155; 502/152; 556/14; 556/22; 556/136; 556/137; 548/101; 548/105; 548/106; 546/2; 546/10; 546/12; 544/225
[58] Field of Search .................... 556/136, 137, 556/14, 22; 502/152, 155; 544/225; 546/2, 10, 12; 548/101, 105, 106

[56] References Cited

U.S. PATENT DOCUMENTS

| | | | |
|---|---|---|---|
| 5,312,940 | 5/1994 | Grubbs et al. | 556/136 |
| 5,342,909 | 8/1994 | Grubbs et al. | 526/171 |
| 5,554,778 | 9/1996 | Beatty et al. | 556/136 |
| 5,710,298 | 1/1998 | Grubbs et al. | 556/22 |
| 5,726,334 | 3/1998 | Beatty et al. | 556/136 |
| 5,728,917 | 3/1998 | Grubbs et al. | 585/653 |
| 5,750,815 | 5/1998 | Grubbs et al. | 585/511 |
| 5,780,701 | 7/1998 | Kaska et al. | 556/137 |
| 5,811,515 | 9/1998 | Grubbs et al. | 556/136 |
| 5,831,108 | 11/1998 | Grubbs et al. | 556/21 |
| 5,849,851 | 12/1998 | Grubbs et al. | 526/93 |
| 5,880,231 | 3/1999 | Grubbs et al. | 526/171 |
| 5,912,376 | 6/1999 | Van Der Schaaf et al. | 556/136 |
| 5,917,071 | 6/1999 | Grubbs et al. | 556/136 |
| 5,919,962 | 7/1999 | Sayo et al. | 556/136 |
| 5,939,504 | 8/1999 | Woodson, Jr. et al. | 556/136 |
| 5,969,170 | 10/1999 | Grubbs et al. | 556/136 |
| 5,977,393 | 11/1999 | Grubbs et al. | 556/137 |

FOREIGN PATENT DOCUMENTS

93/13171  7/1993  WIPO .
96/04289  2/1996  WIPO .

OTHER PUBLICATIONS

R. H. Grubbs et al., Acc. Chem. Res., vol. 28, No. 11, pp. 446–452, 1995.
S. J. Miller et al., J. Am. Chem. Soc., vol. 118, No. 40, pp. 9606–9614, 1996.
D. V. McGrath et al., Organometallics, vol. 13, No. 1, pp. 224–235, 1994.
Journal of Chemical Soc., Chem. Comm. 1994, vol. 22, pp. 2595–2596. B. Weber et al. no month.

*Primary Examiner*—Mark L. Bell
*Assistant Examiner*—J. Pasterczyk
*Attorney, Agent, or Firm*—Luther A. R. Hall

[57] ABSTRACT

Hexacoordinated ruthenium and osmium catalysts of the formulae

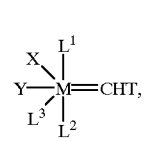

(I)

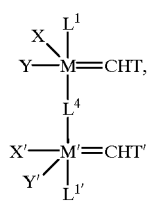

(II)

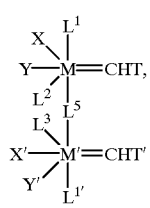

(III)

in which

M and M' independently of one another are ruthenium or osmium;

X, X', Y and Y' independently of one another are anionic ligands, or X and Y and X' and Y' in each case together are bis-anionic ligands $L^1$ and $L^{1'}$ independently of one another are tertiary phosphine;

$L^2$ and $L^3$ independently of one another are a monodentate ligand, or $L^2$ and $L^3$ together are bidentate, neutral electron donor ligands;

$L^4$ is tetradentate, neutral electron donor ligand;

$L^5$ is a bidentate, neutral electron donor ligand; and

T and T' indepedently of one another are H or organic substituents, are useful for the synthesis of custom-tailored polymers and for the ring-closing metathesis of olefins.

4 Claims, No Drawings

HEXACOORDINATED RUTHENIUM OR OSMIUM CARBENE CATALYSTS

The present invention relates to hexacoordinated ruthenium and osmium carbene catalysts, to their preparation and use for synthesizing polymers, for ring-closing metathesis of olefins, for cross-metathesis and for isomerizing olefins.

The thermal metathesis polymerization of cycloolefins which are under ring strain, which has in recent times acquired great importance, requires appropriate catalysts. Whereas use was made first of all of systems comprising catalyst and co-catalyst—see, for example, U.S. Pat. No. 4,060,468 and International Patent Application WO 93/13171—one-component catalysts have also been disclosed [H. H. Thoi et al., *J. Mol. Catal.* 15:245–270 (1982)]. Catalysts of particular interest for the application are so-called metal carbenes, i.e. transition metal compounds, for example ruthenium and osmium compounds, having a group =CR*R** attached to the metal atoms [WO 93/20111; S. Kanaoka et al., *Macromolecules* 28: 4707–4713 (1995); C. Fraser et al., *Polym. Prepr.* 36: 237–238 (1995); P. Schwab et al., *Angew. Chem.* 107: 2179–2181 (1995)]. This type of compound is also suitable for catalyzing ring closure in dienes [WO 96/04289].

The known catalysts are pentacoordinated and contain attached to the metal atoms, in addition to the group =CR*R**, two identical tertiary phosphines as neutral electron donor ligands [WO 93/20111; WO 96/04289].

It has surprisingly been found that hexacoordinated ruthenium and osmium carbenes are excellent catalysts for ring-opening metathesis polymerizations, for other metathesis reactions and for the ring closure of dienes. By an appropriate choice of neutral ligands it is possible to exercise close control over the reactivity, for example the latency, over a wide range.

The invention provides compounds of the formulae

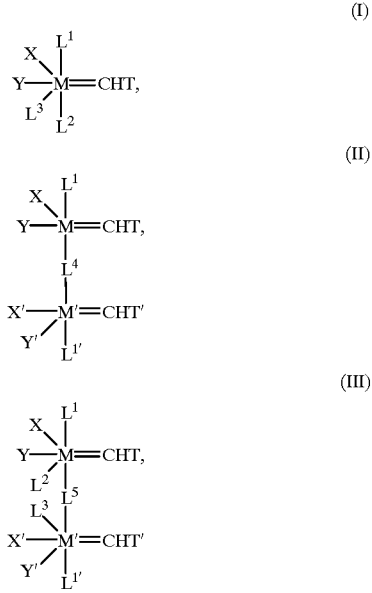

in which
M and M' independently of one another are ruthenium or osmium;
X, X', Y and Y' independently of one another are anionic ligands, or X and Y and X' and Y' in each case together are bis-anionic ligands;
$L^1$ and $L^{1'}$ independently of one another are tertiary phosphine;
$L^2$ and $L^3$ independently of one another are monodentate, or $L^2$ and $L^3$ together are bidentate, neutral electron donor ligands;
$L^4$ is a tetradentate, neutral electron donor ligand;
$L^5$ is a bidentate, neutral electron donor ligand; and
T and T' independently of one another are H, $C_1$–$C_{20}$alkyl, $C_3$–$C_8$cycloalkyl, $C_3$–$C_7$-heterocycloalkyl, $C_6$–$C_{14}$aryl or $C_4$–$C_{15}$heteroaryl, where alkyl, cycloalkyl, heterocycloalkyl, aryl and heteroaryl are unsubstituted or substituted by a substituent from the group consisting of $C_1$–$C_4$alkyl, $C_1$C_4$haloalkyl, $C_1$–$C_4$alkoxy, $C_6$–$C_{10}$aryl, $C_6$–$C_{10}$aryloxy, —$NO_2$ and halogen.

M and M' are preferably ruthenium.

The compounds of the invention have the advantage that dicyclopentadiene (DCPD) is made accessible to thermal metathesis polymerization with a one-component catalyst. It has additionally been found that even linear polybicyclopentadiene can be prepared if the polymerization is conducted in appropriate solvents. Crosslinked polymers are obtained if the polymerization is conducted in bulk. It has also been found that the polymerization takes place even in the presence of polymer additives, such as fillers, for example, and that mouldings, sheets (films) or coatings having excellent physical and mechanical properties are obtained. It was observed, as well, that the compositions comprising DCPD and the compounds of the invention are stable to air and moisture, and thus have high stability on storage. No special protective measures are necessary for the polymerization, which offers considerable advantages in terms of processing. It has also been found that on using these catalysts DCPD can be copolymerized together with other strained cycloolefins as co-monomers. This enables properties to be modified specifically and adapted to the desired purpose of use.

Anionic ligands which are suitable in the context of the present invention are hydride (H⁻), or are derived, for example, from inorganic or organic acids, examples being halide (F⁻, Cl⁻, Br⁻ and I⁻), anions of oxygen acids, $BF_4^-$, $PF_6^-$, $SbF_6^-$ or $AsF_6^-$.

The anions of oxygen acids can, for example, be sulfate, phosphate, perchlorate, perbromate, periodate, antimonate, arsenate, nitrate, carbonate, the anion of a $C_1$–$C_8$-carboxylic acid, such as formate, acetate, propionate, butyrate, benzoate, phenylacetate, mono-, di- or trichloro- or -fluoroacetate, sulfonates, such as methylsulfonate, ethylsulfonate, propylsulfonate, butylsulfonate, trifluoromethylsulfonate (triflate), benzylsulfonate or phenylsulfonate unsubstituted or substituted by $C_1$–$C_4$alkyl, $C_1$–$C_4$alkoxy or halogen, especially fluorine, chlorine or bromine, for example tosylate, mesylate, brosylate, p-methoxy- or p-ethoxyphenylsulfonate, pentafluorophenylsulfonate or 2,4,6-triisopropylsulfonate.

Other suitable anions are $C_1$–$C_{12}$-, preferably $C_1$–$C_6$- and, with particular preference, $C_1$–$C_4$alcoholates, which in particular are branched, for example of the formula $R_xR_yR_zC$—O⁻, in which $R_x$ is H or $C_1$–$C_{10}$alkyl, $R_y$ is $C_1$–$C_{10}$alkyl and $R_z$ is $C_1$–$C_{10}$alkyl or phenyl, and the sum of the carbon atoms of $R_x$, $R_y$ and $R_z$ is at least 2, preferably at least 3 and up to 10. Particular examples are i-propoxy and t-butoxy.

Other suitable anions are $C_3$–$C_{18}$-, preferably $C_5$–$C_{14}$- and, with particular preference, $C_5$–$C_{12}$acetylides, which may have the formula $R_w$—C≡C⁻, in which $R_w$ is $C_1$–$C_{16}$alkyl, preferably α-branched $C_3$–$C_{12}$alkyl, for example of the formula $R_xR_yR_zC$—, or is benzyl or phenyl unsubstituted or substituted by from one to 3 $C_1$–$C_4$alkyl or $C_1$–$C_4$alkoxy substituents. Some examples are i-propyl-, i- and t-butyl-, phenyl-, benzyl-, 2-methyl-, 2,6-dimethyl-, 2-i-propyl-, 2-i-propyl-6-methyl-, 2-t-butyl, 2,6-di-t-butyl- and 2-methyl-6-t-butylphenylacetylide.

Further anionic ligands are organic radicals bearing negative charges, such as $C_1$–$C_{12}$alkyl, e.g. methyl or aralkyl, e.g. benzyl.

Particular preferred anionic ligands are $H^-$, $F^-$, $Cl^-$, $Br^-$, $BF_4^-$, $PF_6^-$, $SbF_6^-$, $AsF_6^-$, $CF_3SO_3^-$, $C_6H_5$—$SO_3^-$, 4-methyl-$C_6H_5$—$SO_3^-$, 3,5-dimethyl-$C_6H_5$—$SO_3^-$, 2,4,6-trimethyl-$C_6H_5$—$SO_3^-$ and 4-$CF_3$—$C_6H_5$—$SO_3^-$ and cyclopentadienyl ($Cp^-$). $Cl^-$ is particularly preferred.

Examples of bis-anionic ligands are the bis-anions of diols, diamines and hydroxy amines, such as catechol, N,N'-dimethyl-1,2-benzenediamine, 2-(methylamino) phenol, 3-(methylamino)-2-butanol and N,N'-bis(1,1-dimethylethyl)-1,2-ethanediamine.

The tertiary phosphines contain preferably 3 to 40, more preferably 3 to 30 and, with particular preference, 3 to 18 carbon atoms. They are peferably of the formula:

$$PR^1R^2R^3 \qquad (IV)$$

in which $R^1$, $R^2$ and $R^3$ independently of one another are $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, where alkyl, cycloalkyl, heterocycloalkyl, aryl, heteroaryl and aralkyl are unsubstituted or substituted by one or more substituents selected from the group consisting of $C_1$–$C_6$alkyl, $C_1$–$C_6$alkoxy, $C_1$–$C_6$haloalkyl, $C_6$–$C_{16}$aryl, —$NO_2$, $SO_3^-$, ammonium or halogen; the radicals $R^1$ and $R^2$ together are tetra- or pentamethylene unsubstituted or substituted by $C_1$–$C_6$alkyl, $C_1$–$C_6$haloalkyl, —$NO_2$ or $C_1$–$C_6$alkoxy and are possibly fused with 1 or 2 bivalent 1,2-phenylene radicals, and $R^3$ is as defined above.

Examples of alkyl are methyl, ethyl and the isomers of propyl, butyl, pentyl, hexyl, heptyl, octyl, nonyl, decyl, undecyl and dodecyl. An example of aryl-substituted alkyl is benzyl. Examples of alkoxy are methoxy, ethoxy and the isomers of propoxy and butoxy.

Some examples of cycloalkyl are cyclobutyl, cycloheptyl, cyclooctyl and, in particular, cyclopentyl and cyclohexyl. Examples of substituted cycloalkyl are methyl-, dimethyl-, trimethyl-, methoxy-, dimethoxy-, trimethoxy-, trifluoromethyl-, bistrifluoromethyl and tris-trifluoromethyl-substituted cyclopentyl and cyclohexyl.

Examples of aryl are phenyl and naphthyl. Examples of aryloxy are phenoxy and naphthyloxy. Examples of substituted aryl are methyl-, dimethyl-, trimethyl-, methoxy-, dimethoxy-, trimethoxy-, trifluoromethyl-, bistrifluoromethyl- or tristrifluoromethyl-substituted phenyl. An example of aralkyl is benzyl. Examples of substituted aralkyl are methyl-, dimethyl-, trimethyl-, methoxy-, dimethoxy-, trimethoxy-, trifluoromethyl-, bistrifluoromethyl- or tristrifluoromethyl-substituted benzyl.

In the context of the present invention heterocycloalkyl comprises one or two and heteroaryl one to four heteroatoms, the heteroatoms being selected from the group consisting of oxygen, sulfur and nitrogen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

Preference is given to compounds of the formula I, II or III in which $L^1$ and $L^{1'}$ independently of one another are tertiary phosphine of the formula IV in which $R^1$, $R^2$ and $R^3$ are identical. Particular preference is given, furthermore, to the radicals $R^1$, $R^2$ and $R^3$ which are sterically bulky, for example cyclic or branched, especially α,α-di-branched and, very particularly, α-branched alkyl groups.

Another group of preferred compounds of the formula I, II or III is formed by those in which $L^1$ and $L^{1'}$ independently of one another are tertiary phosphine of the formula IV in which $R^1$, $R^2$ and $R^3$ independently of one another are $C_1$–$C_{12}$alkyl, $C_5$–$C_8$cycloalkyl, $C_6$–$C_{12}$aryl or $C_7$–$C_{13}$aralkyl, where alkyl, cycloalkyl, aryl and aralkyl are unsubstituted or substituted by one or more substituents selected from the group consisting of $C_1$–$C_4$alkyl, $C_1$–$C_4$alkoxy, $C_1$–$C_4$-haloalkyl, $SO_3^-$ and ammonium.

Within this group, particular preference is given to those in which $R^1$, $R^2$ and $R^3$ independently of one another are $C_1$–$C_8$alkyl, $C_5$- or $C_6$cycloalkyl, $C_6$–$C_{10}$aryl or $C_7$aralkyl, where alkyl, cycloalkyl, aryl and aralkyl are unsubstituted or substituted by one to three substituents selected from the group consisting of methyl, methoxy, ethyl, ethoxy and trifluoromethyl.

Special preference is given to those compounds in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexyl, phenyl, naphthyl or benzyl, e.g. $(i-C_3H_7)_3P$, $(C_5H_9)_3P$ and $(C_6H_{11})_3P$.

Appropriate monodentate, bidentate and tetradentate neutral $e^-$donor ligands are derived, for example, from unsubstituted or substituted heteroarenes such as furan, thiophene, pyrrole, pyridine, bipyridine, picolylimine, γ-pyran, γ-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole.

Examples of substituents are OH, halogen, $C(O)OR_{s1}$, $OC(O)R_{s4}$, $C(O)R_{s2}$, nitro, $NH_2$, cyano, $SO_3M_y$, $OSO_3M_y$, $NR_{20}SO_3M_y$, $N\!=\!N$—$R_{s2}$, $C_1$–$C_{12}$alkyl, $C_2$–$C_{12}$alkenyl, $C_1$–$C_{12}$alkoxy, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_6$–$C_{10}$aryl, $C_6$–$C_{10}$aryloxy, $C_5$–$C_9$heteroaryl, $C_5$–$C_9$heteroaryloxy, $C_7$–$C_{11}$aralkyl, $C_7$–$C_{11}$aralkyloxy, $C_6$–$C_{10}$heteroaralkyl, $C_8$–$C_{11}$aralkenyl, $C_7$–$C_{10}$heteroaralkenyl, monoamino, diamino, sulfonyl, sulfonamide, carbamide, carbamate, sulfohydrazide, carbohydrazide, carbohydroxamic acid residue and aminocarbonylamide, in which $R_{s1}$ is hydrogen, $M_y$, $C_1$–$C_{12}$alkyl, $C_2$–$C_{12}$alkenyl, $C_3$–$C_{12}$cycloalkyl, $C_2$–$C_{11}$heterocycloalkyl, $C_6$–$C_{10}$aryl, $C_5$–$C_9$heteroaryl, $C_7$–$C_{11}$aralkyl or $C_6$–$C_{10}$heteroaralkyl, $R_{s4}$ is hydrogen, $C_1$–$C_{12}$alkyl, $C_2$–$C_{12}$alkenyl, $C_3$–$C_{12}$cycloalkyl, $C_2$–$C_{11}$heterocycloalkyl, $C_6$–$C_{10}$aryl, $C_5$–$C_9$heteroaryl, $C_7$–$C_{11}$aralkyl or $C_6$–$C_{10}$heteroaralkyl, and $R_{s2}$ and $R_{20}$ are hydrogen, $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_6$–$C_{10}$aryl, $C_5$–$C_9$heteroaryl, $C_7$–$C_{11}$aralkyl, $C_6$–$C_{10}$heteroaralkyl, $C_8$–$C_{11}$aralkenyl or $C_7$–$C_{10}$heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, aralkyloxy, heteroaralkyl, aralkenyl and heteroaralkenyl in turn are unsubstituted or substituted by one of the abovementioned substituents; and y is 1 and M is a monovalent metal or y is ½ and M is a divalent metal.

In the context of the description of the present invention, the terms metal and corresponding cations refer to an alkali metal, for example Li, Na or K, an alkaline earth metal, for example Mg, Ca or Sr, or Mn, Fe, Zn or Ag, and corresponding cations. Lithium, sodium and potassium ions, with their salts, are preferred.

NH$_2$, monoamino, diamino, carbamide, carbamate, carbohydrazide, sulfonamide, sulfohydrazide and aminocarbonylamide correspond preferably to a group R$_8$C(O)(NH)$_p$N(R$_9$)—, —C(O)(NH)$_p$NR$_8$R$_9$, R$_8$OC(O)(NH)$_p$N(R$_9$)—, R$_8$R$_{40}$NC(O)(NH)$_p$N(R$_9$)—, —OC(O)(NH)$_p$NR$_8$R$_9$, —N(R$_{40}$)C(O)(N H)$_p$NR$_8$R$_9$, R$_8$S(O)$_2$(NH)$_p$N(R$_9$)—; —S(O)$_2$(NH)$_p$NR$_8$R$_9$; R$_8$R$_{40}$NS(O)$_2$N(R$_9$)— or —NR$_{40}$S(O)$_2$NR$_8$R$_9$, in which R$_8$, R$_9$ and R$_{40}$ independently of one another are hydrogen, OH, C$_1$–C$_{12}$alkyl, C$_1$–C$_{12}$alkenyl, C$_3$–C$_{12}$cycloalkyl, C$_3$–C$_{12}$cycloalkenyl, C$_2$–C$_{11}$heterocycloalkyl, C$_2$–C$_{11}$heterocycloalkenyl, C$_6$–C$_{10}$aryl, C$_5$–C$_9$heteroaryl, C$_7$–C$_{16}$aralkyl, C$_8$–C$_{16}$aralkenyl with C$_2$–C$_6$alkenylene and C$_6$–C$_{10}$aryl, C$_6$–C$_{15}$heteroaralkyl, C$_6$–C$_{15}$heteroaralkenyl, or di-C$_6$–C$_{10}$aryl-C$_1$–C$_6$alkyl, or R$_8$R$_9$N, in which R$_8'$ and R$_9'$ independently of one another are hydrogen, OH, SO$_3$M$_y$, OSO$_3$M$_y$, C$_1$–C$_{12}$alkyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl, C$_6$–C$_{10}$heteroaralkyl, C$_8$–C$_{16}$aralkenyl with C$_2$–C$_6$alkenylene and C$_6$–C$_{10}$aryl, or di-C$_6$–C$_{10}$aryl-C$_1$–C$_6$alkyl, which are unsubstituted or substituted by one or more substituents from the group consisting of OH, halogen, C(O)OR$_{s1}$, OC(O)R$_{s4}$, C(O)R$_{s2}$, nitro, NH$_2$, cyano, SO$_3$M$_y$, OSO$_3$M$_y$, NR$_{20}$SO$_3$M$_y$, C$_1$–C$_{12}$alkyl, C$_2$–C$_{12}$alkenyl, C$_1$–C$_{12}$alkoxy, C$_3$–C$_{12}$cycloalkyl, C$_3$–C$_{12}$cycloalkenyl, C$_2$–C$_{11}$heterocycloalkyl, C$_2$–C$_{11}$heterocycloalkenyl, C$_6$–C$_{10}$aryl, C$_6$–C$_{10}$aryloxy, C$_5$–C$_9$heteroaryl, C$_5$–C$_9$heteroaryloxy, C$_7$–C$_{11}$aralkyl, C$_7$–C$_{11}$aralkyloxy, C$_6$–C$_{10}$heteroaralkyl, C$_8$–C$_{11}$aralkenyl, C$_7$–C$_{10}$heteroaralkenyl, monoamino, diamino, sulfonyl, sulfonamide, carbamide, carbamate, sulfohydrazide, carbohydrazide, carbohydroxamic acid residue and aminocarbonylamide, in which R$_{s1}$ is hydrogen, M$_y$, C$_1$–C$_{12}$alkyl, C$_2$–C$_{12}$alkenyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl or C$_6$–C$_{10}$heteroaralkyl, R$_{s4}$ is hydrogen, C$_1$–C$_{12}$alkyl, C$_2$–C$_{12}$alkenyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl or C$_6$–C$_{10}$heteroaralkyl, and R$_{s2}$ is hydrogen, C$_1$–C$_{12}$alkyl, C$_2$–C$_{12}$alkenyl, C$_3$–C$_{12}$cycloalkyl, C$_3$–C$_{12}$cycloalkenyl, C$_2$–C$_{11}$ heterocycloalkyl, C$_2$–C$_{11}$heterocycloalkenyl, C$_6$–C$_{10}$aryl, C$_5$–C$_9$heteroaryl, C$_7$–C$_{11}$aralkyl, C$_6$–C$_{10}$heteroaralkyl, C$_8$–C$_{11}$aralkenyl or C$_7$–C$_{10}$heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, aralkyloxy, heteroaralkyl, aralkenyl and heteroaralkenyl in turn are unsubstituted or substituted by one of the abovementioned substituents; p is 0 or 1 and y is 1 and M is a monovalent metal or y is ½ and M is a divalent metal; or R$_8$ and R$_9$ or R$_{8'}$ and R$_{9'}$ or R$_8$ and R$_{40}$ in the case of —NR$_8$R$_9$ or —NR$_{8'}$R$_{9'}$ or R$_8$R$_{40}$N— together are tetramethylene, pentamethylene, —(CH$_2$)$_2$—O—(CH$_2$)$_2$—, —(CH$_2$)$_2$—S—(CH$_2$)$_2$— or —(CH$_2$)$_2$—NR$_7$—(CH$_2$)$_2$—, and R$_7$ is H, C$_1$–C$_6$alkyl, C$_7$–C$_{11}$aralkyl, C(O)R$_{s2}$ or sulfonyl.

The sulfonyl substituent is, for example, of the formula R$_{10}$—SO$_2$— in which R$_{10}$ is C$_1$–C$_{12}$alkyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl or C$_6$–C$_{10}$heteroaralkyl which are unsubstituted or substituted by one or more substituents selected from the group consisting of OH, halogen, C(O)OR$_{s1}$, OC(O)R$_{s4}$, C(O)R$_{s2}$, nitro, NH$_2$, cyano, SO$_3$M$_y$, OSO$_3$M$_y$, NR$_{20}$SO$_3$M$_y$, C$_1$–C$_{12}$alkyl, C$_2$–C$_{12}$alkenyl, C$_1$–C$_{12}$alkoxy, C$_3$–C$_{12}$cycloalkyl, C$_3$–C$_{12}$cycloalkenyl, C$_2$–C$_{11}$heterocycloalkyl, C$_2$–C$_{11}$heterocycloalkenyl, C$_6$–C$_{10}$aryl, C$_6$–C$_{10}$aryloxy, C$_5$–C$_9$heteroaryl, C$_5$–C$_9$heteroaryloxy, C$_7$–C$_{11}$aralkyl, C$_6$–C$_{10}$heteroaralkyl, C$_8$–C$_{11}$aralkenyl, C$_7$–C$_{10}$heteroaralkenyl, monoamino, diamino, sulfonyl, sulfonamide, carbamide, carbamate, sulfonhydrazide, carbohydrazide, carbohydroxamic acid residue and aminocarbonylamide, in which R$_{s1}$ is hydrogen, M$_y$, C$_1$–C$_{12}$alkyl, C$_2$–C$_{12}$alkenyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl or C$_6$–C$_{10}$heteroaralkyl, R$_{s4}$ is hydrogen, C$_1$–C$_{12}$alkyl, C$_2$–C$_{12}$alkenyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl or C$_6$–C$_{10}$heteroaralkyl, and R$_{s2}$ and R$_{20}$ are hydrogen, C$_1$–C$_{12}$alkyl, C$_2$–C$_{12}$alkenyl, C$_3$–C$_{12}$cycloalkyl, C$_3$–C$_{12}$cycloalkenyl, C$_2$–C$_{11}$heterocycloalkyl, C$_2$–C$_{11}$heterocycloalkenyl, C$_6$–C$_{10}$aryl, C$_5$–C$_9$heteroaryl, C$_7$–C$_{11}$aralkyl, C$_6$–C$_{10}$heteroaralkyl, C$_8$–C$_{11}$aralkenyl or C$_7$–C$_{10}$heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, heteroaralkyl, aralkenyl and heteroaralkenyl in turn are unsubstituted or substituted by one of the abovementioned substituents; and y is 1 and M is a monovalent metal or y is ½ and M is a divalent metal.

Preferred e$^-$donor ligands are derived, for example, from heteroarenes of the group

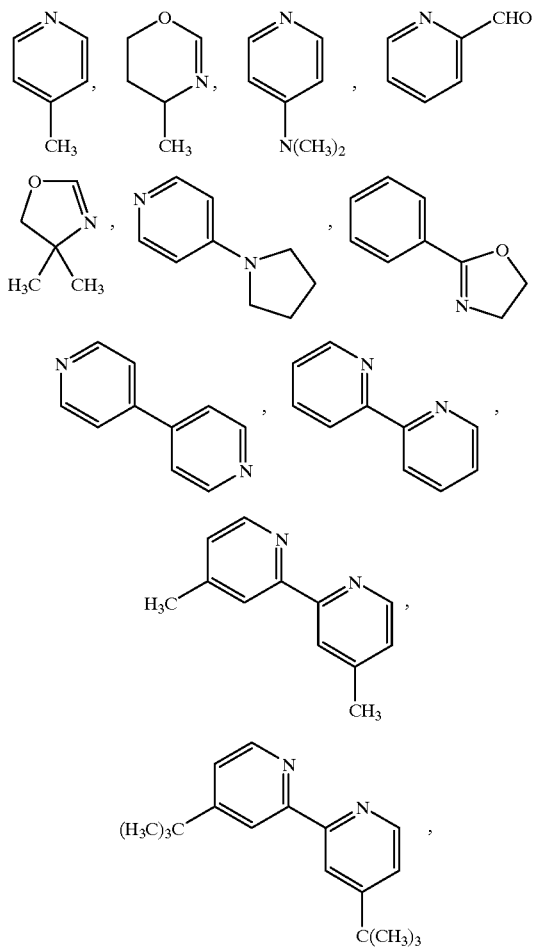

-continued
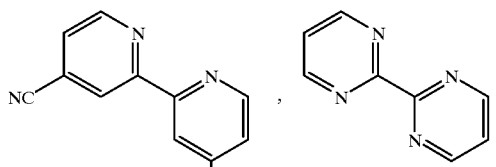
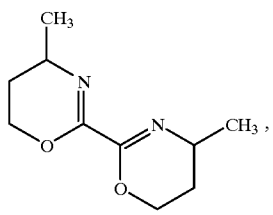
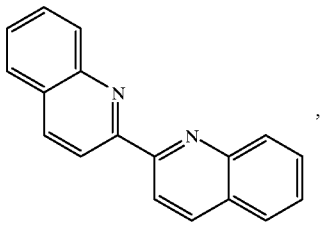
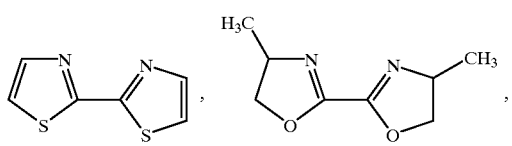
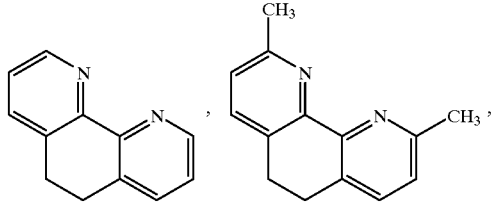
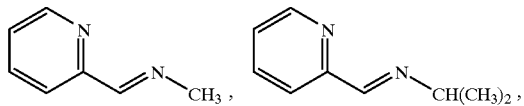
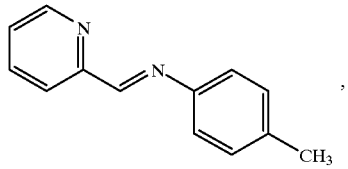
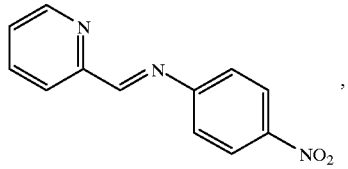
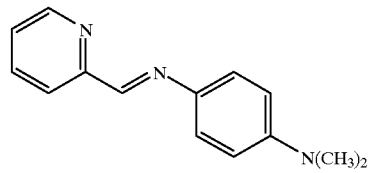
-continued
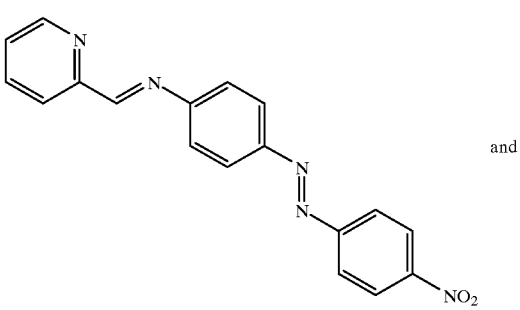
and
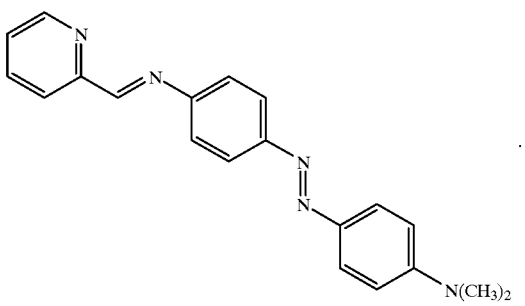
A preferred group of compounds is formed by those compounds of the formula I in which $L^2$ and $L^3$ independently of one another are pyridyl which is unsubstituted or substituted by one or more substituents from the group consisting of $C_1$–$C_{12}$alkyl, $C_2$–$C_{11}$heterocycloalkyl, $C_5$–$C_9$heteroaryl, monoamino, diamino and —C(O)H. Examples are
(1.1)
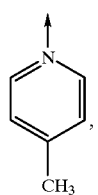
(1.2)
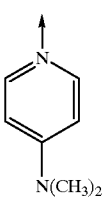
(1.3)
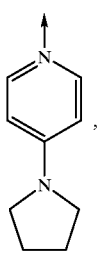

-continued (1.4)

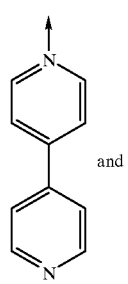

and (1.5)

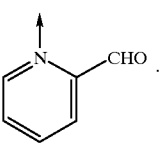

Another preferred group of compounds is formed by those compounds of the formula I in which $L^2$ and $L^3$ together are bipyridyl, phenanthrolinyl, bithiazolyl, bipyrimidinyl or picolylimine which are unsubstituted or substituted by one or more substituents from the group consisting of $C_1$–$C_{12}$alkyl, $C_6$–$C_{10}$aryl and cyano, the substituents alkyl and aryl being in turn unsubstituted or substituted by one or more substituents from the group consisting of $C_1$–$C_{12}$alkyl, nitro, monoamino, diamino and nitro- or diamino-substituted —N=N-$C_6$–$C_{10}$aryl. Examples are (2.1)

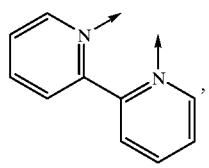

(2.2)

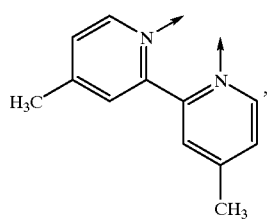

(2.3)

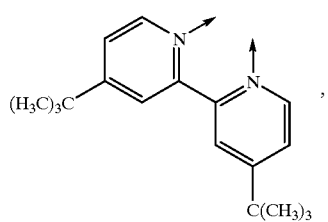

-continued (2.4)

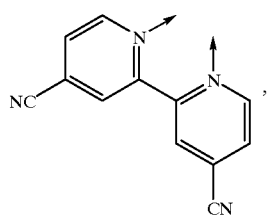

(2.5)

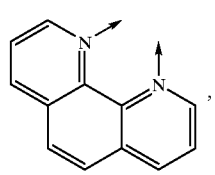

(2.6)

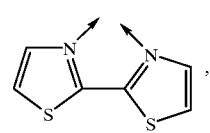

(2.7)

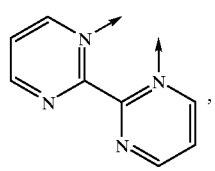

(2.8)

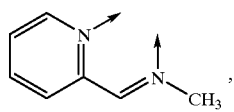

(2.9)

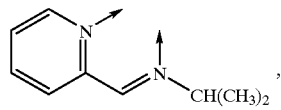

(2.10)

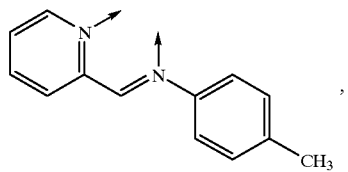

(2.11)

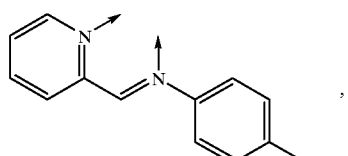

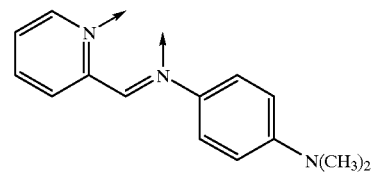
(2.12)

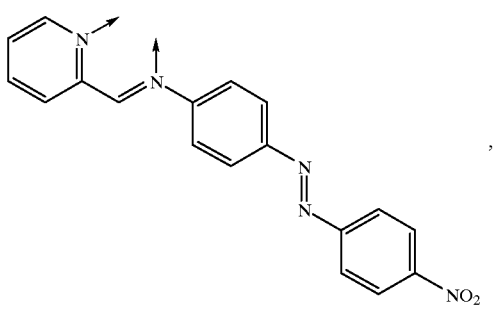
(2.13)

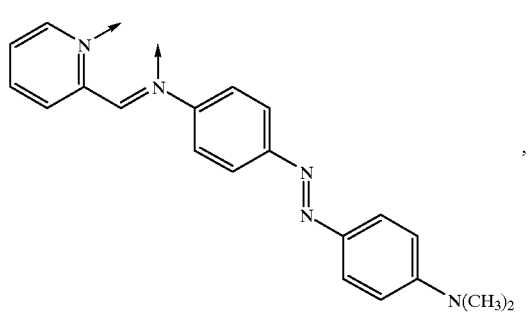
(2.14)

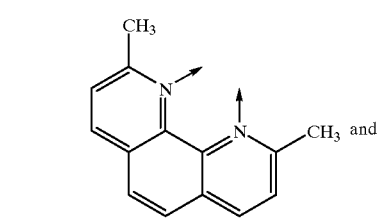
(2.15)

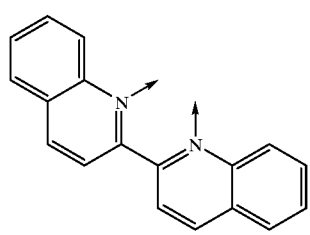
(2.16)

A preferred group of compounds is formed by those compounds of the formula II in which $L^4$ is bipyrimidinyl which is unsubstituted or substituted by one or more substituents from the group consisting of $C_1$–$C_{12}$alkyl, $C_2$–$C_{11}$heterocycloalkyl, $C_5$–$C_9$heteroaryl, monoamino, diamino and —C(O)H. One example is

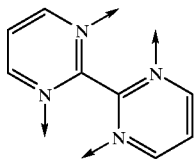
(3.1)

A preferred group of compounds is formed by those compounds of the formula III in which $L^2$ and $L^3$ together and $L^5$ independently thereof are pyridyl which is unsubstituted or substituted by one or more substituents from the group consisting of $C_1$–$C_{12}$alkyl, $C_2$–$C_{11}$heterocycloalkyl, $C_5$–$C_9$heteroaryl, monoamino, diamino and —C(O)H. One example is

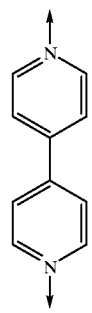
(4.1)

Preference is likewise given to those compounds of the formula I, II or III in which T and T' are unsubstituted or $C_1$–$C_4$alkyl-substituted, especially isopropyl-substituted $C_6$–$C_{14}$aryl, especially phenyl.

A preferred subgroup of the compounds of the formulae I, II and III comprises those of the formulae Ia, IIa and IIIa:

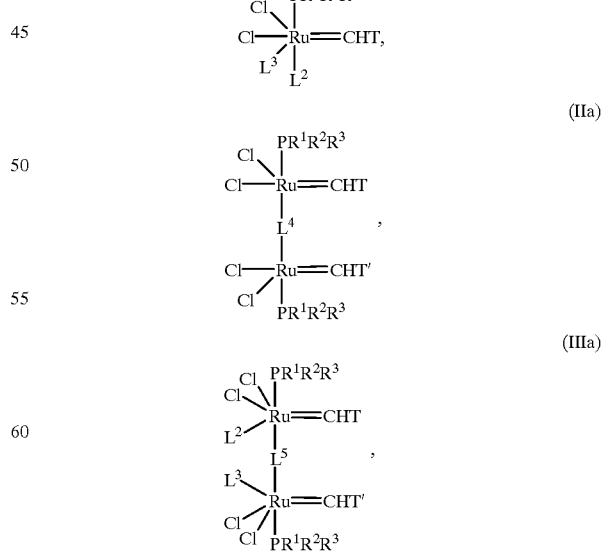

in which $L^2$, $L^3$, $L^4$, $L^5$, $R^1$, $R^2$, $R^3$, T and T' are as defined.

A further preferred subgroup of the compounds of the formulae I, II and III comprises those of the formulae Ia, IIa and IIIa in which $L^2$ and $L^3$ independently of one another are a monodentate, or $L^2$ and $L^3$ together are a bidentate, neutral electron donor ligand;

$L^4$ is a tetradentate neutral electron donor ligand;

$L^5$ is a bidentate neutral electron donor ligand; and

T and T' independently of one another are H, $C_1$–$C_{20}$alkyl, $C_3$–$C_8$cycloalkyl, $C_3$–$C_7$heterocycloalkyl, $C_6$–$C_{14}$aryl or $C_4$–$C_{15}$heteroaryl, where alkyl, cycloalkyl, heterocycloalkyl, aryl and heteroaryl are unsubstituted or substituted by one or more substituents from the group consisting of $C_1$–$C_4$alkyl, $C_1$–$C_4$haloalkyl, $C_1$–$C_4$alkoxy, $C_6$–$C_{10}$aryl, $C_6$–$C_{10}$aryloxy, —$NO_2$ and halogen; and $R^1$, $R^2$ and $R^3$ independently of one another are $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, where alkyl, cycloalkyl, heterocycloalkyl, aryl, heteroaryl and aralkyl are unsubstituted or substituted by one or more substituents selected from the group consisting of $C_1$–$C_6$alkyl, $C_1$–$C_6$alkoxy, $C_1$–$C_6$haloalkyl, $C_6$–$C_{16}$aryl, —$NO_2$, $SO_3^-$, ammonium and halogen; the radicals $R^1$ and $R^2$ together are tetra- or pentamethylene unsubstituted or substituted by $C_1$–$C_6$alkyl, $C_1$–$C_6$haloalkyl, —$NO_2$ or $C_1$–$C_6$alkoxy and possibly fused with 1 or 2 bivalent 1,2-phenylene radicals, and $R^3$ is as defined above.

Particular preference is given to those compounds of the formula Ia, IIa and IIIa in which $L^2$ and $L^3$ independently of one another are pyridyl which is unsubstituted or substituted by one or more substituents from the group consisting of $C_1$–$C_{12}$alkyl, $C_2$–$C_{11}$heterocycloalkyl, $C_5$–$C_9$heteroaryl, monoamino, diamino and —C(O)H; or $L^2$ and $L^3$ together are bipyridyl, phenanthrolinyl, bithiazolyl, bipyrimidinyl, bisquinolinyl or picolylimine which are unsubstituted or substituted by one or more substituents from the group consisting of $C_1$–$C_{12}$alkyl, $C_6$–$C_{10}$aryl and cyano and where the substituents alkyl and aryl are in turn unsubstituted or substituted by one or more substituents from the group consisting of $C_1$–$C_{12}$alkyl, nitro, monoamino, diamino, nitro and diamino-substituted —N=N-$C_6$–$C_{10}$aryl;

$L^4$ is bipyrimidinyl; $L^5$ is bipyridinyl;

T and T' are unsubstituted or $C_1$–$C_4$alkyl-substituted, especially isopropyl- or t-butyl-substituted, $C_6$–$C_{14}$aryl, especially phenyl; and $R^1$, $R^2$ and $R^3$ are isopropyl, cyclopentyl or cyclohexyl.

The present invention additionally provides a process for preparing compounds of the formula I, II or III in which Me and Me' independently of one another are ruthenium or osmium;

X, X', Y, Y', $L^1$, $L^{1'}$, T and T' are as defined, and in order, for example, to prepare compounds in which (a) $L^2$ and $L^3$ independently of one another are a monodentate or together are a bidentate neutral electron donor ligand, a compound of the formula

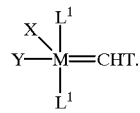

in which X, Y, $L^1$ and T are as defined is reacted with a heteroarene, or (b) $L^4$ is a tetradentate neutral electron donor ligand, a compound of the formula V in which X, Y, $L^1$ and T are as defined is reacted with a heteroarene; or (c) $L^2$ and $L^3$ independently of one another are a monodentate neutral electron donor ligand and $L^5$, independently thereof is a bidentate neutral electron donor ligand, a compound of the formula I in which $L^2$ and $L^3$ independently of one another are a monodentate neutral electron donor ligand is reacted with a compound of the formula V.

The process of the invention is advantageously carried out such that the compounds of the formula V are dissolved in a solvent and then the desired heteroarenes or a compound of the formula I are or is added. The mass ratio of compounds of the formula V to the heteroarene is generally in the range from 1:1 to 1:100, preference being given to a ratio in the range from 1:1 to 1:5. The mass ratio of compounds of the formula V to compounds of the formula I is generally in the range from 1:1 to 1:10, preference being given to a ratio in the range from 1:1 to 1:2. The reaction takes place advantageously at a temperature in the range from –78° C. to 150° C., preferably from 0° C. to 100° C. and, with particular preference, at from room temperature to 50° C.

The invention likewise provides a composition comprising (α) the individual component dicyclopentadiene, or dicyclopentadiene in a mixture with another strained cycloolefin, and (β) a catalytic amount of at least one compound of the formulae I, II or III in which M, M', X, X', Y, Y', $L^1$, $L^{1'}$, $L^2$, $L^3$, $L^4$, $L^5$, T and T' are as defined, with or without further additives for polymers.

Dicyclopentadiene is the dimer of cyclopentadiene, which is known and commercially available and has the formula

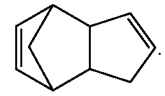

It is known that, together with further cyclopentadiene, dicyclopentadiene forms so-called Diels-Alder adducts and hence forms oligomers which can likewise be used. In accordance with the invention the composition may comprise pure dicyclopentadiene, oligomers of dicyclopentadiene or mixtures thereof. The oligomers are of the formula

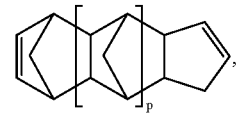

in which p is a number from 1 to 100, preferably from 1 to 50, with particular preference from 1 to 20, and with especial preference from 1 to 10.

The cycloolefins known as strained cycloolefins, which may be present as comonomers in the composition of the invention, are known.

The cyclic olefins can be monocyclic or polycyclic, fused and/or bridged ring systems, which have, for example, from two to four rings and which are unsubstituted or substituted and can contain heteroatoms such as O, S, N or Si, for example, in one or more rings and/or can contain fused aromatic or heteroaromatic rings such as o-phenylene, o-naphthylene, o-pyridinylene or o-pyrimidinylene, for example. The individual cyclic rings may include 3 to 16, preferably 3 to 12, and, with particular preference, 3 to 8 ring members. The cyclic olefins may contain further nonaromatic double bonds, preferably from 2 to 4 such additional double bonds depending on ring size. The ring substituents involved are those which are inert; in other words, those which do not impair the chemical stability of the ruthenium and osmium compounds. The cycloolefins are strained rings or ring systems.

If the cyclic olefins contain more than one double bond, for example 2 to 4 double bonds, then depending on the reaction conditions, on the chosen monomer and on the amount of catalyst it is also possible for crosslinked polymers to form.

Fused-on alicyclic rings contain preferably 3 to 8, more preferably 4 to 7 and with particular preference 5 or 6 ring carbon atoms.

The cyclic olefins which ark present in the composition and can be polymerized with the aid of the catalysts of the invention are known and are described, for example, in WO 96/20235.

The comonomer cycloolefins can be present in an amount of from 0.01 to 99% by weight, preferably 0.1 to 95% by weight, with particular preference from 1 to 90% by weight and, with especial preference, from 5 to 80% by weight, based on the monomers present in the composition. Very particular preference is given to norbornene as comonomer in amounts of, for example, from 20 to 60% by weight.

The dienes which are present in the composition and which can be ring-closed with the aid of the catalysts of the invention are described, for example, in Miller et al. [Miller, S. J., Blackwell, H. E., Grubbs, R. H., *J. Am. Chem. Soc.* 118:9606–9614 (1996)] or in Grubbs et al. [Grubbs, R. H., Miller, S. J., Fu, G. C., *Acc. Chem. Res.* 28:446–452 (1995)].

The catalysts of the invent ion can also be used for isomerizing double bonds, as has already been described for ruthenium-based catalysts in McGrath and Grubbs [McGrath, D. V., Grubbs, R. H., *Organometallics* 13:224 (1994)].

The composition of the invention can comprise inert solvents. One particular advantage is that in the case of liquid monomers metathesis polymerization can be carried out without the use of a solvent. A further advantage is that the polymerization can even be carried out in water, polar and protic solvents or water/ solvent mixtures. In such cases it is of advantage, in the context of the present invention, to use a surfactant.

Examples of suitable inert solvents are protic polar and aprotic solvents, which can be used alone or in mixtures of at least two solvents. Examples are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons, etc.

Compositions of the invention comprising a DCPD and catalyst with or without a cycloolefin are insensitive to oxygen and moisture, which permits storage and reaction without an inert gas.

Catalytic amounts in the context of the present invention denote preferably an amount from 0.001 to 20 mol-%, with particular preference from 0.01 to 15 mol-% and, with very particular preference, from 0.01 to 10 mol-%, based on the amount of monomer. On the basis of high thermocatalytic activity, very particular preference is given to amounts from 0.001 to 2 mol-%.

The composition of the invention which is used for the polymerization can be prepared directly prior to polymerization or can be used as a preformulated mixture, since the catalysts used are of particularly high stability. The mixture may even be stored for a prolonged period prior to polymerization, as a ready-to-use formulation, which is of advantage for large-scale industrial use.

The composition of the intention can comprise additives suitable for polymers, which additives are preferably used as formulation auxiliaries to improve the chemical and physical properties. The auxiliaries, can be present in surprisingly high proportions without adversely affecting the polymerization, for example in amounts of up to 70% by weight, preferably from 1 to 70% by weight, more preferably from 5 to 60% by weight, with particular preference from 10 to 50% by weight and, with especial preference, from 10 to 40% by weight, based on the composition. Such auxiliaries have been disclosed in large numbers and are set out by way of example in the following list of auxiliaries:

1. Antioxidants 1.1. Alkylated monophenols

For example 2,6-di-tert-butyl-4-methylphenol, 2-butyl-4, 6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or sidechain-branched nonylphenols; such as 2,6-di-nonyl-4-methylphenol, 2,4-dimethyl-6-(1'-methylundec-1'-yl)-phenol, 2,4-dimethyl-6-(1'-methylheptadec-1'-yl)-phenol, 2,4-dimethyl-6-(1'-methyltridec-1'-yl)phenol and mixtures thereof.

1.2. Alkylthiomethylphenols

For example 2,4-dioctylthiomethyl-6-tert-butylphenol, 2,4-dioctylthiomethyl-6-methylphenol, 2,4-dioctylthiomethyl-6-ethylphenol, 2,6-didodecyl-thiomethyl-4-nonylphenol.

1.3. Hydroquinones and Alkylated Hydroquinones

For example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols

For example α-tocopherol, β-tocopherol, γ-tocopherol, δ-tocopherol and mixtures thereof (vitamin E).

1.5. Hydroxylated Thiodiphenyl Ethers

For example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols

For example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-(butylphenol), 2,2'- ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl Compounds

For example 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl 3,5-di-tert-butyl-4-hydroxybenzylmercaptoacetate.

1.8. Hydroxybenzylated Malonates

For example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecyl mercaptoethyl-2,2-bis(3,5-di-tert-butyl-4-hydroxybenzyl)malonate, di-[4-(1,1,3,3-tetramethylbutyl)phenyl] 2,2-bis(3,5-di-tert-butyl-4-hydroxybenzyl)malonate.

1.9. Aromatic Hydroxybenzyl Compounds

For example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds

For example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates

For example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols

For example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic Acid

With mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic Acid

With mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β(3,5-dicyclohexyl-4-hydroxyphenyl) propionic Acid

With mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl Acetic Acid

With mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic Acid

E.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 from Uniroyal).

1.18. Ascorbic Acid (Vitamin C).

1.19. Aminic Antioxidants

For example N,N'-diisopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethyl-butyl)-N'-phenyl-p)-phenylenediamine, N-(1-methyl-heptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'- di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diamino-diphenylmethane, 1,2-di[(2-methyl-phenyl)amino]ethane, 1,2-di(phenylamino) propane, (o-tolyl)biguanide, di-[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialylated nonyldiphenylamines, a mixture of mono- and dialkylated dodecyldiphenylamines, a mixture of mono- and dialkylated isopropyl/isohexyl-diphenylamines, mixtures of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one and 2,2,6,6-tetramethylpiperidin-4-ol.

2. UV Absorbers and Light Stabilizers 2.1. 2-(2'-Hydroxyphenyl)benzotriazoles

For example 2-(2'-hydroxy-5'-methylphenyl) benzotrizole, 2-(3',5'-di-tert-butyl-2'-hydroxyphenyl) benzotriazole, 2-(5'-tert-butyl-2'-hydroxyphenyl) benzotriazole, 2-(2'-hydroxy-5'-(1,1,3,3-tetramethylbutyl) phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzptriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl] benzotriazole with polyethylene glycol 300;

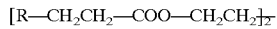

where R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones

For example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of Substituted or Unsubstituted Benzoic Acids

For example 4-tert-butyl-phenyl salicylate, phenyl salicylate, octylphenyl salicylate, dibenzoylresorcinol, bis (4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates

For example ethyl α-cyano-β,β-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-(β-carbomethoxy-βcyanovinyl)-2-methylindoline.

2.5. Nickel Compounds

For example nickel complexes of 2,2'-thiobis[4-(1,1,3,3-tetramethylbutyl)phenol], such as the 1:1 or 1:2 complex, with or without additional ligands such as n-butylamine, triiathanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically Hindered Amines

For example bis(2,2,6,6-tetramethylpiperidin-4-yl) sebacate, bis(2,2,6,6-tetramethylpiperidin-4-yl)succinate, bis(1,2,2,6,6-pentamethylpiperidin-4-yl)sebacate, bis(1-octyloxy-2,2,6,6-tetramethylpiperidin-4-yl)sebacate, bis(1, 2,2,6,6-pentamethylpiperidyl)n-butyl-3,5-di-tert-butyl-4-hydroxybenzylmalonate, the condensate of 1-hydroxyethyl-2,2,6,6-tetramethyl-4-hydroxypiperidine and succinic acid, the linear or cyclic condensates of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the linear or cyclic condensates of N,N'-bis-(2,2, 6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5- dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)-hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2, 2,6,6-tetramethyl-4-piperidyl)-n-dodecylsuccinimide, N-(1, 2,2,6,6-pentamethyl-4-piperidyl)-n-dodecylsuccinimide, 2-undecyl-7,7,9,9-tetramethyl-1-oxa-3,8-diaza-4-oxospiro [4.5]decane, the reaction product of 7,7,9,9-tetramethyl-2- cycloundecyl-1-oxa-3,8-diaza-4-oxospiro[4.5]decane and epichlorohydrine, 1,1-bis(1,2,2,6,6-pentamethyl-4-piperidyloxycarbonyl)-2-(4-methoxyphenyl)ether, N,N'-bisformyl-N,N'-bis(2,2,6,6-tetramethyl-4-piperidyl)-hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine.

2.7. Oxalamides

For example 4,4'-dioctyloxyoxanilide, 2,2'-diethoxy-oxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl) oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy- and of o- and p-ethoxy-disubstituted oxanilides.

2.8. 2-(2-Hydroxyphenyl)-1,3,5-triazines

For example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal Deactivators

For example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl) thiopropionyl dihydrazide.

4. Phosphites, Phosphines and Phosphonites

For example triphenyl phosphite, diphenyl alkyl phosphites, phenyl dialkyl phosphites, tris(nonylphenyl) phosphite, trilauryl phosphite, trioctadecyl phosphite, trimethylphosphine, tri-n-butylphosphine, triphenylphosphine, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyldibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyl-tris(3,3',5,5"tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite.

Particular preference is given to using the following phosphites:

Tris(2,4-di-tert-butylphenyl)phosphite (Irgafos®168, Ciba-Geigy), tris(nonylphenyl)phosphite, (A)
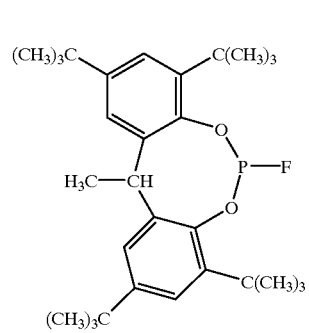

(B)
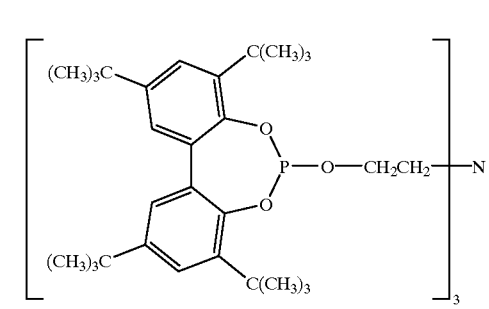

(C)
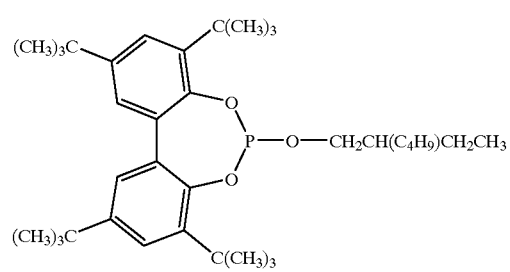

(D)
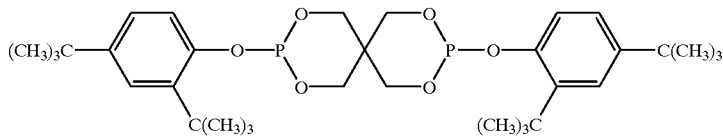

(E)
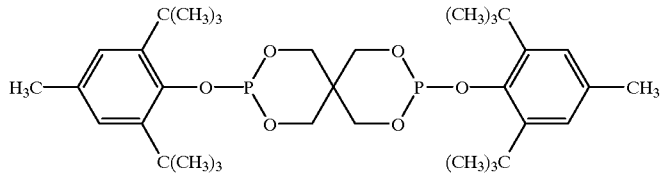

(F)
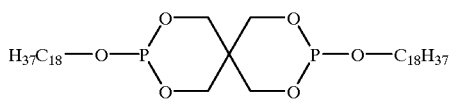

(G)
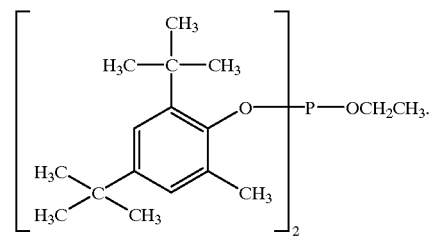

5. Hydroxylamines

For example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones

For example N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alpha-heptadecyl nitrone, N-octadecyl alpha-pentadecyl nitrone, N-heptadecyl alpha-heptadecyl nitrone, N-octadecyl alpha-hexadecyl-nitrone, and nitrones derived from N,N-dialkylhydroxylamin(es prepared from hydrogenated tallow fatty amines.

7. Thiosynergists

For example dilauryl thiodiproprionate or distearyl thiodipropionate.

8. Peroxide Scavengers

For example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate.

9. Polyamide Stabilizers

For example copper salts in combination with iodides and/or phosphorus compounds and salts of divalent manganese.

10. Basic Co-stabilizers

For example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating Agents

For example inorganic substances, such as talc, metal oxides such as titanium dioxide or magnesium oxide, phosphates, carbonates or sulfates of, preferably, alkaline earth metals; organic compounds such as mono- or polycarboxylic acids and their salts, such as 4-tert-butylbenzoic acid, adipic acid, diphenyl acetic acid, sodium succinate or sodium benzoate; and polymeric compounds, for example ionic copolymers (ionomers).

12. Fillers and Reinforcing Agents

For example calcium carbonate, silicates, glass fibres, glass beads, talc, kaolin, mica, barium sulfate, metal oxides and hydroxides, carbon black, graphite, wood flour and flours or fibres of other natural products, and synthetic fibres.

13. Other Additives

For example plasticizers, lubricants, emulsifiers, pigments, rheological additives, catalysts, levelling assistants, optical brighteners, flameproofing agents, antistatic agents, blowing agents.

14. Benzofuranones and Indolinones

As described, for example, in U.S. Pat. Nos. 4,325,863; 4,338,244; 5,175,312, 5,216,052; 5,252,643; DE-A-4316611; DE-A-4316622; DE-A-4316876; EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The invention provides, furthermore, a process for preparing metathesis polymers, which comprises heating a composition comprising (α') the individual component dicyclopentadiene, or dicyclopentadiene in the mixture with a strained cycloolefin, and (β') a catalytic amounit of at least one compound of the formulae I, II and III having the above definitions in a mixture with further additives for polymers and, if desired, subjecting the obtainable metathesis polymer to a shaping process.

The process of the invention is preferably carried out at a temperature of at least 0° C. In particular, the process of the invention is conducted at temperatures from 0° to 300° C., preferably at from room temperature to 250° C., with particular preference from room temperature to 200° C. and, with especial preference, at from room temperature to 160° C. Following polymerization it may be advantageous to condition the polymers at elevated temperatures, for example from 80 to 200° C. To prepare linear polymers the reaction is preferably carried out in dilute solutions.

Polymerization can be associated with shaping processes such as calandering, casting, compression moulding, injection moulding or extrusion, for example. With the process of the invention it is possible to produce materials for the machining production of shaped articles or thermoplastically deformable materials for producing mouldings of all kinds and coatings. Advantageously, shaping and polymerization are connected in solvent-free reactive systems, it being possible to employ processing techniques such as injection moulding, extrusion, polymerization in predetermined forms (possibly under superatmospheric pressure), for example.

The invention also provides the polymers obtainable by the process of the invention.

Of the polymers, preference is given to those containing only carbon and hydrogen.

The polymers prepared by the process of the invention can be homopolymers or copolymers with random distribution of the structural units, graft polymers or block polymers, and crosslinked polymers of this kind. They may have an average molecular weight ($\overline{Mw}$) of, for example, from 500 to 2 million daltons, preferably from 1000 to 1 million daltons (determined by GPC by comparison with polystyrene standards of narrow distribution).

It has surprisingly been found that the polymerization leads in high yields to a polydicyclopentadiene which corresponds to a linear polymer or copolymer having structural units of the formula

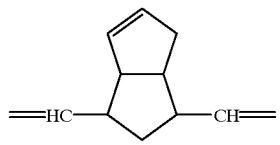

and represents a preferred subject of the invention. A further preferred subject of the invention comprises crosslinked copolymers having structural units of the formula

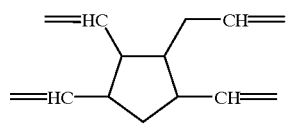

which can be prepared by the process of the invention.

The uncrosslinked or linear polymers comprise oligomers and polymers and can contain, for example, from 5 to 5000, advantageously from 10 to 2000, preferably from 20 to 1000, with particular preference from 20 to 500 and, with especial preference, from 20 to 300 structural units. Where the polymers are processed further preference is given to relatively low molecular weights, and in the case of processing to mouldings use is judiciously made of polymers having relatively high molecular weights.

Depending on the nature and amount of the monomers used, the polymers of the invention may have different properties. Some are notable for very high oxygen permeability, excellent dielectric properties (low dielectric constants, low loss factors or tan δ values), good thermal stability (glass transition temperatures above 100° C.), good toughnesses (impact and notched impact strength), flexibility and mechanical strengths (fracture resistance), hardness and low water absorption. Others have outstanding optical properties, such as high transparency and low reflective indices, for example. Also deserving of emphasis are the low shrinkage and the excellent surface properties (smoothness, gloss, adhesion). They can therefore be used in a very wide variety of industrial fields.

As coats on the surface of carrier materials, the polymers of the invention are notable for high adhesive strength. In addition, the coated materials are notable for high surface smoothness and gloss. Among the good mechanical properties particular emphasis should be placed on the low shrinkage and high impact strength, but also the thermal stability. Also deserving of mention are the ease of demoulding and the high solvent resistance. The surfaces can be modified further, for example painted or printed, and the high adhesive strengths of the coatings should be mentioned in this case, too.

The polymers obtainable in accordance with the invention are particularly suitable for producing articles of all kinds, such as mouldings for cars, boats, leisure articles, pallets, pipes, sheets, etc.; as insulating materials for producing electrical and electronic components; as implants; as binders for coating materials; as heat-curable compositions for modelling or as adhesives for bonding substrates having low surface energies (TEFLON, polyethylene or polypropylene). The compositions of the invention can also be used to prepare coatings by thermal polymerization, it being possible to use both clear (transparent) and even pigmented compositions. Both white and colour pigments can be used. The production of mouldings by thermoplastic shaping processes for articles of all kinds should also be mentioned.

The compositions of the invention are also suitable in particular for producing protective coats. The invention also provides a variant of the process of the invention for producing coated materials, in which the composition of the invention is applied with or without solvent as a film to a carrier, for example by dipping, brushing, flow coating, rolling, knife coating or spin coating techniques, the solvent (if used) is removed, and the film is heated for polymerization. With this process it is possible to modify or protect the surfaces of substrates (corrosion protection).

The present invention provides, furthermore, a coated carrier material, wherein a coat of the polymer of the invention is applied to a substrate.

The present invention likewise provides a coated substrate having a cured film of the polymer of the invention.

Examples of suitable substrates (carrier materials) are those of glass, minerals, ceramics, plastics, wood, semimetals, metals, metal oxides and metal nitrides. The film thicknesses depend essentially on the desired use and can, for example, be from 0.1 to 1000 μm, preferably from 0.5 to 500 μm and, with particular preference, from 1 to 100 μm. The coated materials are notable for high adhesive strength and good thermal and mechanical properties.

The coated materials of the invention can be prepared by known methods such as brushing, knife coating, flow coating methods such as curtain coating or spin coating.

In the case of coatings, particularly good results are often achieved if the thermal metathesis polymerization is carried out with the additional use of cycloolefins which in addition contain from 1 to three, and preferably one, further double bonds and which in the context of the invention are polycyclic fused ring systems.

The examples which follow illustrate the invention.

A) Preparing the Catalysts

Catalysts of the formulae I, II and III are prepared as described in the following examples. The numbers in the definitions of $L^2$, $L^3$, $L^4$ and $L^5$ relate to the examples of neutral electron donor ligands given above; $C_6H_{11}$: cyclohexyl; $C_5H_9$: cyclopentyl; $C_3H_7$: isopropyl. The physical data are collated in Tables 1–4. The following text contains preparation instructions for some selected compounds.

TABLE 1

Compounds of the formula Ia in which $L^2$ and $L^3$ independently of one another are monodentate ligands

| Comp. No. | $L^2$ | $L^3$ | T | $PR^1R^2R^3$ | $^1$H NMR$^a$ δ carbene ($J_{PH}$) | Elemental analysis [%] | | | | |
|---|---|---|---|---|---|---|---|---|---|---|
| | | | | | | C | H | Cl | N | Ru |
| 1.1 | 1.1 | 1.1 | Phenyl | $P(C_6H_{11})_3$ | 20.22 (11.6) | 61.14 | 7.50 | 9.95 | 3.98 | 13.67 |
| 1.2 | 1.2 | 1.2 | Phenyl | $P(C_6H_{11})_3$ | 19.83 (12.2) | 59.71 | 7.81 | 9.18 | 7.33 | 12.56 |
| 1.3 | 1.2 | 1.2 | 4-Isopropylphenyl | $P(C_6H_{11})_3$ | 19.80 (11.9) | 60.61 | 7.75 | 8.44 | 6.51 | 11.96 |
| 1.4 | 1.2 | 1.2 | Phenyl | $P(C_5H_9)_3$ | 20.10 (12.4) | 62.98 | 6.84 | 8.75 | 6.78 | 12.39 |
| 1.5 | 1.3 | 1.3 | Phenyl | $P(C_6H_{11})_3$ | 19.95 (12.1) | 62.34 | 6.60 | 8.41 | 6.38 | 12.04 |
| 1.6 | 1.5 | 1.5 | Phenyl | $P(C_6H_{11})_3$ | 20.21 (11.4) | 63.42 | 6.63 | 9.51 | 6.77 | 11.70 |
| 1.7 | 1.5 | 1.5 | Phenyl | $P(C_6H_{11})_3$ | 20.75 (n.d.)$^b$ | 58.89 | 6.65 | 9.27 | 3.54 | 13.19 |
| 1.8 | 1.1 | 1.1 | Phenyl | $P(C_3H_7)_3$ | 20.36 (11.3) | 55.42 | 6.97 | 11.51 | 4.73 | 16.54 |
| 1.9 | 1.2 | 1.2 | Phenyl | $P(C_3H_7)_3$ | 20.25 (11.7) | 54.17 | 7.26 | 10.60 | 4.08 | 15.06 |

$^a$NMR in CDCl$_3$; δ in ppm; $J_{PH\ in\ Hz}$;
$^b$n.d.: not determined.

TABLE 2

Compounds of the formula Ia in which $L^2$ and $L^3$ together are bidentate ligands

| Comp. No. | $L^2 + L^3$ | T | $PR^1R^2R^3$ | $^1$H NMR$^a$ δ carbene ($J_{PH}$) | Elemental analysis [%] | | | | |
|---|---|---|---|---|---|---|---|---|---|
| | | | | | C | H | Cl | N | Ru |
| 2.1 | 2.1 | Phenyl | $P(C_6H_{11})_3$ | 19.26 (10.1) | 60.32 | 6.86 | 10.08 | 4.14 | 14.39 |
| 2.2 | 2.1 | 4-tert-Butylphenyl | $P(C_6H_{11})_3$ | 19.52 (12.4) | 62.23 | 7.47 | 9.35 | 3.75 | 13.31 |
| 2.3 | 2.2 | Phenyl | $P(C_6H_{11})_3$ | 18.67 (15.7) | 60.98 | 6.99 | 9.81 | 3.88 | 13.98 |
| 2.4 | 2.3 | 4-tert-Butylphenyl | $P(C_6H_{11})_3$ | 19.49 (12.2) | 65.34 | 8.07 | 8.43 | 3.09 | 11.51 |
| 2.5 | 2.4 | Phenyl | $P(C_6H_{11})_3$ | 19.52 (12.1) | 59.55 | 6.23 | 9.64 | 7.39 | 13.32 |
| 2.6 | 2.5 | Phenyl | $P(C_6H_{11})_3$ | 21.68 (9.5) | 61.35 | 6.76 | 9.67 | 3.62 | 13.81 |
| 2.7 | 2.5 | 4-tert-Butylphenyl | $P(C_6H_{11})_3$ | 21.49 (9.0) | 63.41 | 7.37 | 9.34 | 3.84 | 13.13 |
| 2.8 | 2.6 | Phenyl | $P(C_6H_{11})_3$ | 19.50 (n.d.)$^b$ | 52.56 | 6.29 | 9.83 | 4.08 | 14.06 |
| 2.9 | 2.7 | Phenyl | $P(C_6H_{11})_3$ | 19.52 (12.0) | 56.74 | 6.62 | 10.01 | 8.13 | 14.33 |
| 2.10 | 2.7 | 4-Isopropylphenyl | $P(C_6H_{11})_3$ | 19.26 (11.9) | 58.44 | 7.10 | 9.73 | 4.41 | 13.83 |
| 2.11 | 2.8 | Phenyl | $P(C_6H_{11})_3$ | 19.68 (n.d.)$^b$ | 58.17 | 7.25 | 10.61 | 4.05 | 15.13 |
| 2.12 | 2.9 | Phenyl | $P(C_6H_{11})_3$ | 19.54 (n.d.)$^b$ | 59.17 | 7.58 | 10.46 | 4.27 | 14.48 |
| 2.13 | 2.10 | Phenyl | $P(C_6H_{11})_3$ | 18.83 (12.3) | 61.94 | 6.87 | 9.81 | 3.86 | 13.57 |
| 2.14 | 2.11 | 4-Isopropylphenyl | $P(C_6H_{11})_3$ | 18.44 (12.2) | 59.67 | 6.33 | 8.69 | 5.42 | 12.39 |
| 2.15 | 2.12 | 4-Isopropylphenyl | $P(C_6H_{11})_3$ | 18.79 (12.7) | 61.95 | 7.60 | 8.73 | 5.16 | 12.44 |
| 2.16 | 2.13 | Phenyl | $P(C_6H_{11})_3$ | 18.82 (12.5) | 59.34 | 6.18 | 8.35 | 7.86 | 11.71 |
| 2.17 | 2.13 | 4-isopropylphenyl | $P(C_6H_{11})_3$ | 18.54 (12.1) | 60.52 | 6.51 | 7.91 | 7.85 | 11.22 |
| 2.18 | 2.14 | 4-isopropylphenyl | $P(C_6H_{11})_3$ | 18.69 (n.d.)$^b$ | 62.93 | 7.19 | 7.60 | 7.51 | 11.20 |
| 2.19 | 2.34 | Phenyl | $P(C_6H_{11})_3$ | 19.48 (12.2) | 64.93 | 7.77 | 8.34 | 3.25 | 11.88 |
| 2.20 | 2.10 | Phenyl | $P(C_3H_7)_3$ | 18.94 (12.1) | 56.50 | 6.61 | 11.28 | 4.39 | 16.24 |

TABLE 2-continued

Compounds of the formula Ia in which $L^2$ and $L^3$ together are bidentate ligands

| Comp. No. | $L^2 + L^3$ | T | $PR^1R^2R^3$ | $^1$H NMR$^a$ δ carbene ($J_{PH}$) | Elemental analysis [%] C | H | Cl | N | Ru |
|---|---|---|---|---|---|---|---|---|---|
| 2.21 | 2.9 | Phenyl | $P(C_3H_7)_3$ | 19.28 (12.2) 18.16 (13.5)$^c$ | 52.51 | 6.74 | 12.18 | 4.78 | 17.53 |
| 2.22 | 2.2 | 4-isopropylphenyl | $P(C_6H_{11})_3$ | 19.60 (n.d.) | 62.32 | 7.63 | 9.08 | 3.47 | 12.95 |
| 2.23 | 2.5 | Phenyl | $P(C_3H_7)_3$ | 19.95 (14.1) | 55.70 | 8.36 | 11.93 | 4.90 | 16.52 |
| 2.24 | 2.13 | Phenyl | $P(C_3H_7)_3$ | 18.89 (n.d.)$^b$ | 54.34 | 5.60 | 9.67 | 9.14 | 13.56 |
| 2.25 | 2.2 | Phenyl | $P(C_3H_7)_3$ | 19.80 (11.7) | 55.27 | 6.68 | 11.53 | 4.53 | 16.82 |
| 2.26 | 2.7 | Phenyl | $P(C_6H_{11})_3$ | 19.30 (12.0) | 56.50 | 6.63 | 9.89 | 8.14 | 14.57 |
| 2.27 | 2.7 | 4-isopropylphenyl | $P(C_3H_7)_3$ | 19.26 (11.9) | 58.41 | 6.81 | 9.72 | 7.42 | 13.47 |
| 2.28 | 2.16 | 4-tert-butylphenyl | $P(C_6H_{11})_3$ | 19.76 (<0.3) | 66.31 | 7.15 | 8.50 | 3.07 | 11.61 |
| 2.29 | 2.15 | Phenyl | $P(C_6H_{11})_3$ | 19.12 (n.d.)$^b$ | 62.18 | 6.67 | 9.55 | 3.50 | 13.24 |

$^a$NMR in CDCl$_3$; δ ppm; $J_{PH}$ in Hz;
$^b$n.d.: not determined;
$^c$two isomers

TABLE 3

Compounds of the formula IIa in which $L^4$ is a tetradentate ligand

| Comp. No. | $L^4$ | T = T' | $PR^1R^2R^3$ | $^1$H NMR$^a$ δ carbene ($J_{PH}$) | Elemetal analysis [%] C | H | Cl | N | Ru |
|---|---|---|---|---|---|---|---|---|---|
| 3.1 | 3.1 | 4-Isopropylphenyl | $P(C_6H_{11})_3$ | 19.50 (n.d.)$^b$ 19.67 (n.d.)$^b$ | 58.11 | 7.43 | 10.53 | 4.05 | 15.06 |
| 3.2 | 3.1 | 4-Phenyl | $P(C_6H_{11})_3$ | 19.60 (n.d.)$^b$ 19.80 (n.d.)$^b$ | 56.24 | 7.04 | 11.62 | 4.36 | 16.04 |

$^a$NMR in CDCl$_3$; δ in ppm; $J_{PH}$ in Hz;
$^b$n.d.: not determined

TABLE 4

Compounds of the formula IIIa in which $L^5$ and $L^{5'}$ independently of one another are bidentate ligands

| Comp. No. | $L^4$ | T = T' | $PR^1R^2R^3$ | $^1$H NMR$^a$ δ carbene ($J_{PH}$) | Elemental analysis [%] C | H | Cl | N | Ru |
|---|---|---|---|---|---|---|---|---|---|
| 4.1 | 4.1 | Phenyl | $P(C_6H_{11})_3$ | 19.80 (n.d.)$^b$ | 60.01 | 6.92 | 10.35 | 4.10 | 14.58 |

$^a$NMR in CDCl$_3$; δ in ppm; $J_{PH}$ in Hz;
$^b$n.d.: not determined

EXAMPLE A1

Preparing the Catalyst 1.5

200 mg of $RuCl_2(\!=\!CH\!-\!C_6H_5)P(C_6H_{11})_3$ are dissolved in 10 ml of $CH_2Cl_2$. At room temperature (RT) 5 equivalents of compound No. 1

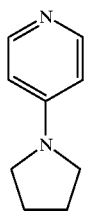

(1)

are added. After stirring at RT for 30 minutes, the reaction mixture is concentrated in vacuo and the residue is washed with hexane (3×5 ml each time) and dried in vacuo. The pure product is obtained in virtually quantitative yield.

$^1$H: 19.95 (d, 1, $J_{PH}$=12.1 Hz, carbene-H);8.30, 8.07, 7.98, 7.56, 7.20, 6.36, 6.12 (d, d, d, m, m, d, d, 13, pyrrolidinopyridine-H and phenyl-H); 3.27 (m, 16, pyrrolidino-H); 2.1–1.2 (m, 33, $PCy_3$).

EXAMPLE A2

Preparing Catalyst 2.2

200 mg of $RuCl_2(\!=\!CH\!-\!C_6H_4\!-\!4\!-\!C(CH_3)_3)P(C_6H_{11})_3$ and 5 equivalents of compound No. 2

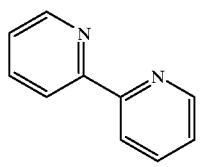

(2)

are used to give, by the method of Example A1, the pure product in virtually quantitative yield.

$^1$H: 19.52 (d, 1, $J_{PH}$=12.4 Hz, carbene-H); 9.90, 8.88, 8.66, 8.51, 8.38, 8.17, 8.01, 7.81, 7.63, 7.49, 7.30, 7.05 (d, d, d, d, d, d, d, t, t, m, d, m, t, 12, phenyl-H and bipyridine-H); 1.8–0.9 (m, 42, t-Bu and PCy$_3$).

EXAMPLE A3

Preparing Catalyst 2.6

200 mg of RuCl$_2$(=CH—C$_6$H$_5$)P(C$_6$H$_{11}$)$_3$ and 5 equivalents of compound No. 3

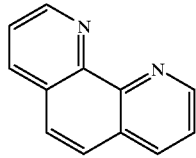

(3)

are used to give, by the method of Example A1, the pure product in virtually quantitative yield.

$^1$H: 21.68 (d, 1, $J_{PH}$=9.5 Hz, carbene-H); 10.0, 9.0, 8.6, 8.46, 8.17, 7.96, 7.87.5, 7.3 (m, 13, phenanthroline-H and plienyl-H); 2.1–1.0 (m, 33, PCy$_3$).

EXAMPLE A4

Preparing Catalyst 2.4

200 mg of RuCl$_2$(=CH—C$_6$H$_4$-4-C(CH$_3$)$_3$)P(C$_6$H$_{11}$)$_3$ and 5 equivalents of compound No. 4

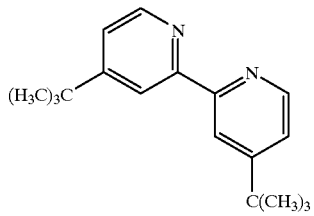

(4)

are used to give, by the method of Example A1, the pure product in virtually quantitative yield.

$^1$H: 19.49 (d, 1, $J_{PH}$=12.2 Hz, carbene-H); 9.77, 8.86, 8.31, 8.4, 7.98, 7.65, 7.47, 7.08 (d, d, d, s, s, d, d, d, 10, phenyl-H and bipyridine-H); 1.8–0.9 (m, 60, 3×t-Bu and PCy$_3$). $^{31}$P: 35.9

EXAMPLE A5

Preparing Catalyst 2.3

200 mg of RuCl$_2$(=CH—C$_6$H$_5$)P(C$_6$H$_{11}$)$_3$ and 5 equivalents of compound No. 5

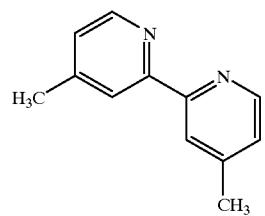

(5)

are used to give, by the method of Example A1, the pure product in virtually quantitative yield.

$^1$H: 18.67 (d, 1, $J_{PH}$=15.7 Hz, carbene-H); 9.5–6.4 (m, 11, phenyl-H and bipyridine-H); 2.7–1.2 (m, 39, PCy$_3$ and bipyridine-methyl).

EXAMPLE A6

Preparing Catalyst 1.1

200 mg of RuCl$_2$(=CH—C$_6$H$_5$)P(C$_6$H$_{11}$)$_3$ and 5 equivalents of compound No. 6

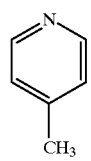

(6)

are used to give, by the method of Example A1, the pure product in virtually quantitative yield.

$^1$H: 20.22 (d, 1, $J_{PH}$=11.6 Hz, carbene-H); 8.91, 8.12, 7.1, 6.75 (4 br s, 8, pyridine-H); 8.03, 7.52, 7.15 (d, t, d, 5, phenyl-H); 2.35–1.15 (m, 39, PCy$_3$ and pyridine-methyl). $^{31}$P: 34.0

B) Practical Examples

B1 Polymerizations of DCPD 0.3% by weight of catalylst is added to DCPD (94% from Shell, degassed). Curing conditions: 1 h at 80° C., 1 h at 100° C., 2 h at 120° C. ΔH and T$_g$ measurements by DSC (Differential Scanning Calorimetry), weight loss measurement by TGA (Thermogravimetric Analysis) to 300° C.

TABLE 5

| Comp. No. | Onset Temperature[a] | ΔH [J/g] | T$_g$ [° C.] | Weight loss [%] |
|---|---|---|---|---|
| 1.1 | <20 | 249 | 135 | 3.0 |
| 1.2 | 40 | 334 | 96 | 6.4 |
| 1.4 | 50 | 284 | 31 | 13.8 |
| 1.5 | 40 | 298 | 82 | 14.5 |
| 1.9 | 30 | 376 | 56 | 6.9 |

[a]Temperature at which gelling begins.

B2 Polymerizations of Norbornene 500 mg of norbornene are dissolved in 10 ml of THF, 1.0% by weight of catalyst is added, and, following the indicated reaction time, reaction is quenched with one drop of vinyltrimethylsilane. The molecular weights and the polydispersity were determined by GPC.

TABLE 6

| Comp. No. | Reaction time/ temperature | Yield [%] | $M_w[\times 10^3]$ | $M_w/M_n$ |
|---|---|---|---|---|
| 2.3 | 5 min./20° C. | 66 | 973 | 2.56 |
| 1.8 | 2 h/20° C. | 98 | 154 | 1.35 |
| 1.9 | 2 h/20° C. | 98 | 145 | 1.74 |
| 2.9 | 5 min./20° C. | 96 | 1063 | 1.98 |
| 2.12 | 5 min./20° C. | 86 | 641 | 2.44 |
| 2.13 | 2 h/20° C. | 82 | 389 | 2.91 |
| 2.14 | 5 min./20° C. | 88 | 618 | 2.33 |
| 2.15 | 2 h/20° C. | 80 | 560 | 2.74 |
| 2.20 | 10 h/60° C. | 88 | 356 | 2.75 |
| 2.23 | 10 h/60° C. | 14 | 321 | 1.99 |

$M_w$: ponderal mean of the molecular weight distribution
$M_n$: numerical mean of the molecular weight distribution

What is claimed is:

1. A compound of one of the formulae

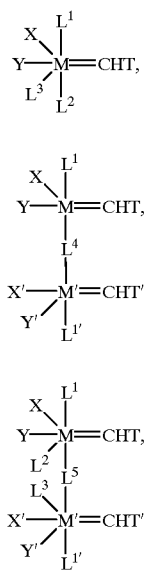

in which
M and M' independently of one another are ruthenium or osmium;
X, X', Y and Y' independently of one another are anionic ligands, or X and Y and X' and Y' in each case together are bis-anionic ligands;
$L^1$ and $L^{1'}$ independently of one another are tertiary phosphine;
$L^2$ and $L^3$ independently of one another are a monodentate ligand, or $L^2$ and $L^3$ together are bidentate, neutral electron donor ligand;
$L^4$ is a tetradentate, neutral electron donor ligand;
$L^5$ is a bidentate, neutral electron donor ligand; and
T and T' independently of one another are H, $C_1-C_{20}$alkyl, $C_3-C_8$cycloalkyl, $C_3-C_7$heterocycloalkyl, $C_6-C_{14}$aryl or $C_4-C_{15}$heteroaryl, where alkyl, cycloalkyl, heterocycloalkyl, aryl and heteroaryl are unsubstituted or substituted by a substituent selected from the group consisting of $C_1-C_4$alkyl, $C_1-C_4$haloalkyl, $C_1-C_4$alkoxy, $C_6-C_{10}$aryl, $C_6-C_{10}$aryloxy, —$NO_2$ and halogen.

2. A compound according to claim 1 wherein M and M' are ruthenium.

3. A compound according to claim 1 which is one of the formulae

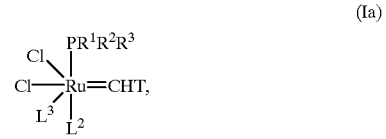

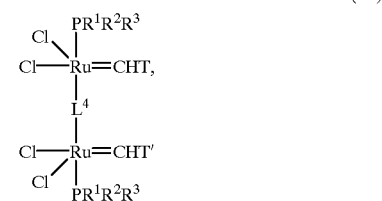

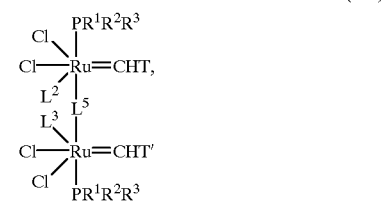

in which
$L^2$, $L^3$, $L^4$, $L^5$, T and T' are as defined in claim 1, and
$R^1$, $R^2$ and $R^3$ independently of one another are $C_1-C_{20}$alkyl, $C_4-C_{12}$cycloalkyl, $C_2-C_{11}$heterocycloalkyl, $C_6-C_{16}$aryl, $C_2-C_{15}$heteroaryl or $C_7-C_{16}$aralkyl, where alkyl, cycloalkyl heterocycloalkyl, aryl, heteroaryl and aralkyl are unsubstituted or substituted by one or more substituents selected from the group consisting of $C_1-C_6$alkyl, $C_1-C_6$alkoxy, $C_1-C_6$haloalkyl, $C_6-C_{16}$aryl, —$NO_2$, $SO_3^-$, ammonium and halogen;
or the radicals $R^1$ and $R^2$ together are tetramethylene or pentamethylene, unsubstituted or substituted by $C_1-C_6$alkyl, $C_1-C_6$haloalkyl, —$NO_2$ or $C_1-C_6$alkoxy, or are fused with 1 or 2 bivalent 1,2-phenylene radicals;
and $R^3$ is $C_1-C_{20}$alkyl, $C_4-C_{12}$cycloalkyl, $C_2-C_{11}$heterocycloalkyl, $C_6-C_{16}$aryl, $C_2-C_{15}$heteroaryl or $C_7-C_{16}$aralkyl, where alkyl, cycloalkyl, heterocycloalkyl, aryl, heteroaryl and aralkyl are unsubstituted or substituted by one or more substituents selected from the group consisting of $C_1-C_6$alkyl, $C_1-C_6$alkoxy, $C_1-C_6$haloalkyl, $C_6-C_{16}$aryl, —$NO_2$, $SO_3^-$, ammonium and halogen.

4. A compound according to claim 3 which is one of the formulae Ia, IIa and IIIa in which $L^2$ and $L^3$ independently of one another are pyridine which is unsubstituted or substituted by one or more substituents selected from the group consisting of $C_1-C_{12}$alkyl, $C_2-C_{11}$heterocyloalkyl, $C_5-C_9$heteroaryl, monoamino, diamino and —C(O)H; or
$L^2$ and $L^3$ together are bipyridyl, phenanthrolinyl, bithiazolyl, bipyrimidinyl, bisquinolinyl or picolylimine which are unsubstituted or substituted by one or more substituents selected from the group consisting of $C_1-C_{12}$alkyl, $C_6-C_{10}$aryl and cyano, and where the substituents alkyl and aryl are in turn unsubstituted or substituted by one of more substituents selected from the group consisting of $C_1-C_{12}$alkyl, nitro, monoaminio, diamino and diamino-substituted —N=N-$C_6-C_{10}$aryl;
$L^4$ is bipyrimidinyl;

$L^5$ is bipyridinyl;

T and T' are unsubstituted $C_6$–$C_{14}$aryl or $C_1$–$C_4$alkyl-substituted $C_6$–$C_{14}$aryl; and $R^1$, $R^2$ and $R^3$ are isopropyl, cyclopentyl or cyclohexyl.

* * * * *